United States Patent
Hendi et al.

(10) Patent No.: US 9,463,510 B2
(45) Date of Patent: *Oct. 11, 2016

(54) NOBLE METAL NANOPARTICLES, METHOD FOR PREPARING THE SAME AND THEIR APPLICATION

(71) Applicant: King Saud University, Riyadh (SA)

(72) Inventors: Awatif Ahmed Hendi, Riyadh (SA); Manal A. Awad, Riyadh (SA); Nada E. Eisa, Riyadh (SA); Khaled M. Ortashi, Riyadh (SA)

(73) Assignee: King Saud University, Riyadh (SA)

( * ) Notice: Subject to any disclaimer, the term of this patent is extended or adjusted under 35 U.S.C. 154(b) by 109 days.

This patent is subject to a terminal disclaimer.

(21) Appl. No.: 14/485,821

(22) Filed: Sep. 15, 2014

(65) Prior Publication Data
US 2015/0148870 A1    May 28, 2015

(30) Foreign Application Priority Data

Nov. 27, 2013   (EP) .................................... 13194693

(51) Int. Cl.
| | |
|---|---|
| *B22F 9/24* | (2006.01) |
| *A61K 33/38* | (2006.01) |
| *A61N 5/06* | (2006.01) |
| *A61K 33/24* | (2006.01) |
| *B22F 1/00* | (2006.01) |
| *B82Y 40/00* | (2011.01) |
| *B82Y 5/00* | (2011.01) |

(52) U.S. Cl.
CPC ................. *B22F 9/24* (2013.01); *A61K 33/24* (2013.01); *A61K 33/38* (2013.01); *A61N 5/0625* (2013.01); *B22F 1/0018* (2013.01); *B22F 2301/25* (2013.01); *B22F 2304/054* (2013.01); *B82Y 5/00* (2013.01); *B82Y 40/00* (2013.01); *Y10S 977/773* (2013.01); *Y10S 977/81* (2013.01); *Y10S 977/896* (2013.01); *Y10S 977/915* (2013.01); *Y10T 428/2982* (2015.01)

(58) Field of Classification Search
None
See application file for complete search history.

(56) References Cited

U.S. PATENT DOCUMENTS

2012/0055873 A1    3/2012   Hoag et al.

OTHER PUBLICATIONS

Jing-Liang Li et al: "Gold-Nanoparticle-Enhanced Cancer Photothermal Therapy", IEEE Journal of Selected Topics in Quantum Electronics, IEEE Service Center, vol. 16, No. 4, Oct. 6, 2009, pp. 989-996.
European Search Report for corresponding Application No. 13194693.1 dated Jun. 18, 2014.

*Primary Examiner* — Robert A Wax
*Assistant Examiner* — Randeep Singh
(74) *Attorney, Agent, or Firm* — Renner, Otto, Boisselle & Sklar, LLP

(57) ABSTRACT

The present invention discloses a method for preparing noble metal nanoparticles, comprising the following steps: a) preparing an *Olea Europaea* fruit extract; b) preparing an *Acacia Nilotica* extract; c) mixing the *Olea Europaea* fruit extract and the *Acacia Nilotica* extract for preparing a mixed extract; d) providing an aqueous solution containing a noble metal compound dissolved therein; e) mixing the mixed extract obtained in step c) and the aqueous solution of step d) to form noble metal nanoparticles; noble metal nanoparticles obtained thereby and their use.

16 Claims, 14 Drawing Sheets

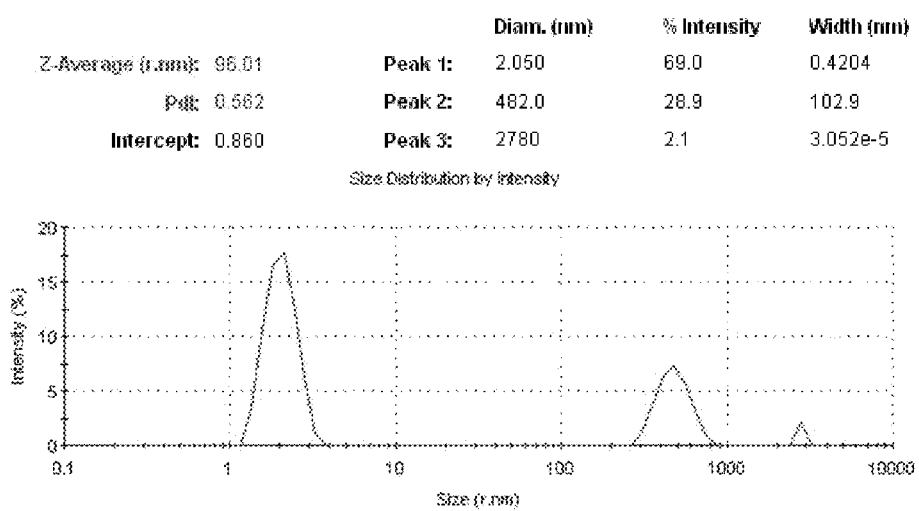
Fig. 7
Fig. (8a)

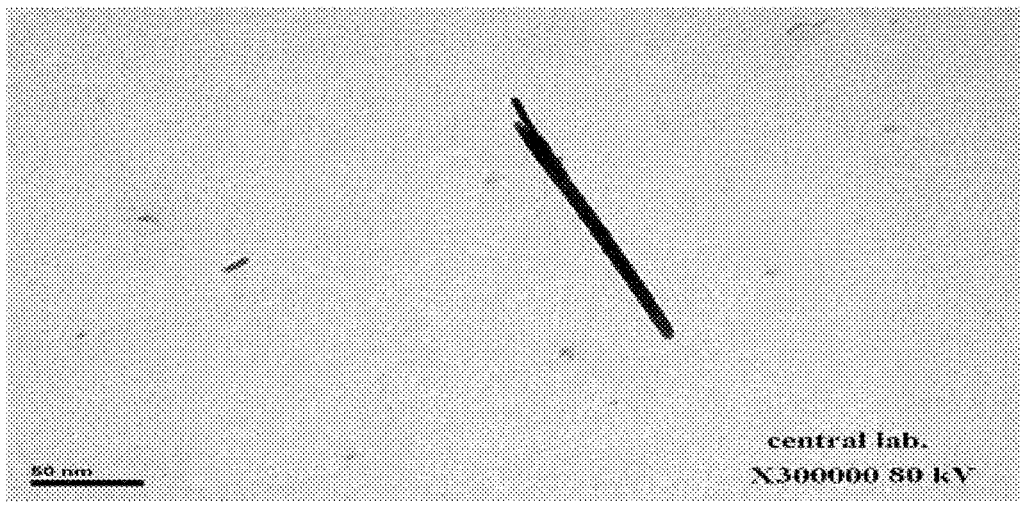
Fig. (8b)
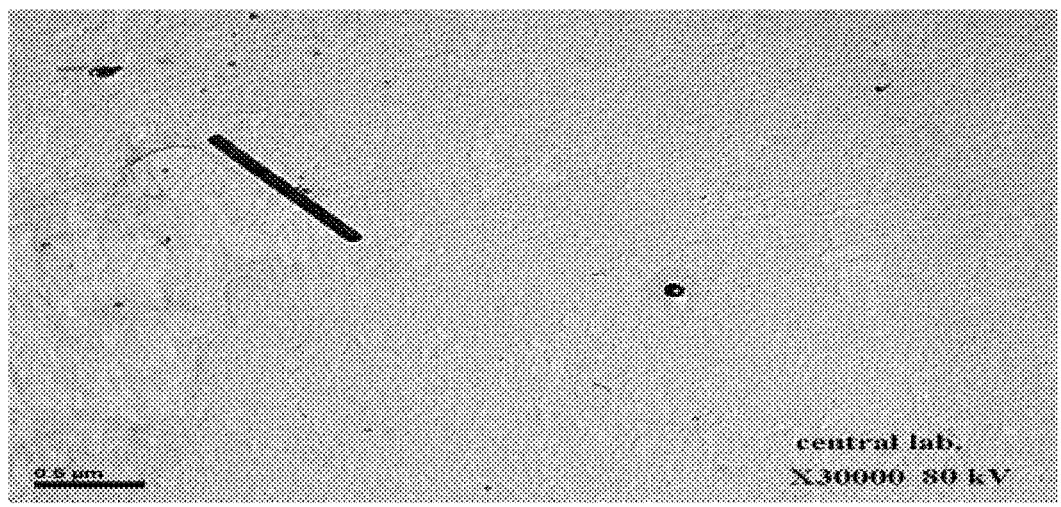
Fig. (8c)

NOBLE METAL NANOPARTICLES,
METHOD FOR PREPARING THE SAME AND
THEIR APPLICATION

CROSS-REFERENCE TO RELATED
APPLICATION AND PRIORITY CLAIM

This application is related to and claims priority under 35 U.S.C. §119(a) to European Application No. 13194693.1, filed 27 Nov. 2013, titled "Noble Metal Nanoparticles, Method for Preparing the Same and Their Application", the entirety of which is hereby incorporated herein by reference.

TECHNICAL FIELD

The present invention relates to noble metal nanoparticles, a method for preparing the same, and their use.

BACKGROUND

Nanoparticles are of great scientific interest as they can be utilized in many industrial or medical applications. Nanoparticles are typically sized between 1 to 100 nm.

In particular, gold nanoparticles have been intensively studied as they are versatile materials having interesting chemical, electronic and optical properties for a broad range of different applications. The properties and applications of gold nanoparticles strongly depend on their respective shape and size.

Possible applications of gold nanoparticles lie, for example, in the fields of nanoelectronics, imaging, sensing, catalysis, optics, environmental industry, energy development and biomedicine. Due to the low oxidation metal potential of gold nanoparticles, they can be used in medical diagnostic tests, such as labeling, X-ray contrasting, immunestrain and phago kinetic tracking studies, in targeted truck delivery techniques, as well as in medical therapies.

Silver nanoparticles have various and important applications. Historically, silver has been known to have a disinfecting effect and has been found in applications ranging from traditional medicines to culinary items. It has been reported that silver nanoparticles (AgNPs) are non-toxic to humans and most effective against bacteria, virus and other eukaryotic micro-organism at low concentrations and without any side effects. Moreover, several salts of silver and their derivatives are commercially manufactured as antimicrobial agents. In small concentrations, silver is safe for human cells, but lethal for microorganisms. Antimicrobial capability of AgNPs allows them to be suitably employed in numerous household products such as textiles, as well as disinfection in water treatment, food storage containers, home appliances and in medical devices. The most important application of silver and AgNPs is in medical industry such as tropical ointments to prevent infection against burns and open wounds.

Several methods for producing noble metal nanoparticles have been developed which utilize harsh conditions. Wet methods often require the application of aggressive reducing agents, for example sodium borohydride, capping agents and may additionally need organic solvents such as toluene or chloroform. Furthermore, often toxic compounds must be employed or are produced during the synthesis of noble nanoparticles. Although known methods may produce successfully noble metal nanoparticles, energy preparation consumption and pollution effects are relatively high, as well as materially and environmental costs. Even the availability of some materials, in particular of biomaterials, as for example plant materials, may be a problem. In consequence, there remains a need for more cost-effective and environmentally benign alternative methods for producing noble metal nanoparticles with improved properties on a large scale. Main criteria for a green chemistry synthesis of stabilized nanoparticles are the choice of eco-friendly and non-hazardous solvents, reducing agents and capping agents, especially for noble metal nanoparticles which shall be utilized in medical treatment.

Biological synthesis of nanoparticles by plant extracts is at present under exploitation as some researchers worked on it and tested then for antimicrobial activities.

Chemical reduction methods are widely used for synthesizing Ag—NPs because of their readiness to generate Ag—NPs under gentle conditions and their ability to synthesize Ag—NPs on a large scale.

US 2010/0055199 A1 discloses systems and methods for synthesizing silver nanoparticles using *Trichoderma funghi*. In an aspect, *Trichoderma reesei* was used for extracellular synthesis of silver nanoparticles. In the biosynthesis of metal nanoparticles by a fungus, one or more enzymes or metabolites are produced that reduce the silver ions to its metallic solid nanoparticles through a catalytic process.

US 2010/0200501 A1 relates to methods of making and using as well as compositions of metal nanoparticles formed by green chemistry synthetic techniques. The production of metal nanoparticles of Ag, Au, Pt, Pd, Fe, Mn, Cu and In in a single pot method using plant extracts as coffee and/or tee extract and use of these metal nanoparticles in removing contaminates from soil, groundwater and other contaminated sites are described. The reducing agent used for the preparation of the metal nanoparticles can be among others a phenolic compound or a flavonoid or a combination thereof.

For the last two decades extensive work has been done to develop new drugs from natural products because of the resistance of micro-organisms to the existing drugs. Nature has been an important source of products currently being used in medical practice.

There are various strategies for using gold nanoparticles as a drug delivery vehicle, including systems based on covalent binding or drug encapsulation. Furthermore, it has been reported that antibiotics often disturb the bacterial flora of digestive tract which may develop multiple drug-resistant isolates, hence novel ways of formulating biocide materials is an upcoming field of attraction. For this reason, there is a need for the use of an agent which does not generate resistance and presents a good bactericidal property. Gold nanoparticles have a great bactericidal effect on several ranges of microorganisms.

A number of synthetic methods have been employed for the synthesis of silver-based nanoparticles involving physical, chemical and biochemical techniques. However, these chemical synthesis methods employ toxic chemicals in the synthesis route which may have adverse effect in the medical applications and hazard to environment.

SUMMARY

Therefore, preparation of Ag—NPs by green synthesis approach has advantages over physical and chemical approaches as it is environmental friendly, cost effective and the most significant advantage is that conditions of high temperature, pressure, energy and toxic chemicals are not required in the synthesis protocol.

It is an object of the present invention to provide a method for preparing noble metal nanoparticles using green chemistry synthetic techniques which overcomes the drawbacks of the prior art. Especially, a method shall be provided which allows the use of non-toxic, abundant eco-friendly bioavailable material and which enables saving energy and costs. It is a further object to provide noble metal nanoparticles which show improved medical properties and can be utilized in industrial and medical applications.

The first object is achieved by a method for preparing noble metal nanoparticles, comprising the following steps: a) preparing an *Olea Europaea* fruit extract; b) preparing an *Acacia Nilotica* extract; c) mixing the *Olea Europaea* fruit extract and the *Acacia Nilotica* extract for preparing a mixed extract; d) providing an aqueous solution containing a noble metal compound dissolved therein; e) mixing the mixed extract obtained in step c) and the aqueous solution of step d) to form noble metal nanoparticles.

By the term "nanoparticle" is meant a microscopic particle with at least one dimension less than 100 nm.

Preferably, the mixed extract obtained in step c) contains flavonoids, phenols and/or pentacyclic triterpenoids as effective group.

Within the present application, the term "effective group" is to be understood, that the effective group containing compound of the mixed extract plays a main role, for example, as reducing and/or stabilizing agent for the inventive noble metal nanoparticles. One or more different effective group(s) may be alone or together responsible for these effects.

It is preferred that the preparation of the *Olea Europaea* fruit extract is performed by adding deionized or distilled water to *Olea Europaea* fruit, preferably grinding it and then filtering the extract.

In a preferred embodiment, the preparation of the *Acacia Nilotica* extract is performed by adding deionized or distilled water to *Acacia Nilotica*, preferably soaking it and then filtering the extract.

Alternatively, the term "extract" of the present invention means an extract obtained from bioavailable plant and/or fruit materials. The extract may be obtained by using standard extraction techniques, like a separatory funnel, a soxhlet apparatus and so on. Further, the extraction may comprise one or more different extraction steps in which the same or different extraction techniques may be used.

More preferably, the *Olea Europaea* fruit extract and the *Acacia Nilotica* extract are mixed in a range of mixing ratios from 5:1 to 1:5, preferably in ratios of 7:3, 3:1, 1:1 or 1:3.

It is also preferred that the mixing in step e) includes stirring at 25° C., putting the mixture into a shaker for 30 min at 145 rpm, shaking the mixture in a water bath at 125 rpm at 60° C. or leaving the mixture for about 3 months at room temperature.

More preferably, the mixing of step e) is preferably at room temperature.

According to the present invention, any mixing technique utilized in the art may be used.

Even preferred, the noble metal is selected from Au or Ag.

It is further preferred that the gold nanoparticles shall be prepared by utilizing an inorganic acid containing Chloroauric Acid ($HAuCl_4$). When silver nanoparticles shall be prepared, a solution of silver nitrate may be utilized and provided in step d).

Most preferably, the aqueous solution provided in step d) also comprises a surfactant, preferably cetyl trimethyl ammonium bromide (CTAB). Especially the noble metal nanoparticles prepared in the presence of a surfactant, which are preferably colloidal noble metal nanorods, are effective as antibacterial agent.

The second object is achieved by noble metal nanoparticles prepared by the inventive method wherein the average particle size is within a range of 10-100 nm, preferably of 20-60 nm, more preferably the average particle size is 40 nm.

It is further preferred that the noble metal nanoparticles are substantially spherical. Even preferred, the noble metal nanoparticles obtained have a smooth surface morphology, i.e. regular shapes and morphology.

In a further embodiment, the noble metal nanoparticles are substantially monodispersed.

More preferably, the gold nanoparticles are colloidal.

In another preferred embodiment, the nanoparticles are in the form of nanorods, having preferably an average size of 96 nm.

A further object is achieved by the use of the inventive noble metal nanoparticles in a catalytic, electronic, imaging, sensing, photonic, energy, optical, environmental, biotechnical or medical application.

More preferably, the noble metal nanoparticles are preferably used in antibacterial and cancer treatment, and more preferably are used with photothermal therapy in treatment of Ehrlich Ascites carcinoma cells.

It was also found that the inventive noble metal nanoparticles can be used in textile fabrication, in food storage containers, as antibacterial agent against *Kleb, pseudomonas, salmonella* and *Escherichia coli* bacteria, in nanoelectronics, as biosensors, as biomedical tools, in sustainable energy development, in bioremediation of radioactive wastes, as functional electrical coating, in the synthesis of enzyme electrodes and particularly in medicine, such as for delivery of antigen for vaccination, gene delivery for treatment or prevention of genetic disorder, and drug delivery, in waste water treatment etc.

Surprisingly, it was found that the inventive method provides the possibility to synthesize noble metal nanoparticles in an easy, energy saving and cost-efficient way from non-toxic, abundant natural materials and medical plants. In addition, the synthesis method of the invention is accomplished in a short time and is suitable for large scale preparation. Moreover, it was found that the inventive method allows faster nanoparticle growth, the possibility to achieve a variety of particle shapes and a better control of particle size distribution, compared to the prior art US 2010/0055199A1. The inventive noble metal nanoparticles may have several applications, such as antibacterial and cancer treatment, catalyst in chemical reactions, electrical batteries, in spectrally selective coatings for absorption of solar energy, as optical elements, in pharmaceutical components, chemical sensing, biosensing or in food and water storage.

This invention focuses especially on a new method for synthesis of gold nanorods and nanospheres. The preferred presence of surfactant molecules on the surface of the gold nanorods and nanospheres strongly influences their reactivity and stability. The preparation of Au nanorods and nanospheres according to the invention has advantages over physical and chemical approaches as it is eco-friendly, economical, clean and doesn't involve the use of any toxic chemical, as well as simple application and storage at room temperature and high stability. Further, the antibacterial efficacy of inventive gold nanorods and nanospheres was studied against various strains of *Escherichia coli, Staphylococcus aureus,* and conjugated with antibiotic ampicillin, and the results shows that eco-friendly gold nanorods and nanospheres showed highly effective antibacterial activity towards Gram-positive and Gram-negative microorganisms and also with antibiotic, examined by the agar-well-diffusion method.

Preparation of Ag—NPs by the inventive method has advantages over physical and chemical approaches as it is environmental friendly, cost effective and the most significant advantage is that conditions of high temperature, pressure, energy and toxic chemicals are not required in the synthesis protocol.

BRIEF DESCRIPTION OF THE DRAWINGS

The invention is now further illustrated by the accompanying figures and detailed description from which further features and advantages may be taken. It is to be noted that the following explanations are presented for the purpose of illustration and description only; they are not intended to be exhaustive or to limit the invention to the precise form disclosed.

FIG. 7 presents a graph of a Zetasizer® for measuring the average size of nanorods prepared according to the present invention, example 2.

FIGS. 8a, 8b and 8c present a graph of transition electron microscopy (TEM) image of gold nanorods synthesized according to the invention, with different magnifications.

DETAILED DESCRIPTION

Example 1

Colloidal gold nanoparticles were synthesized by bioreduction of $AuCl_4^-$ ions. 15 g *Olea Europaea* fruit was washed carefully and was added to 15 ml deionized water. Then it was grinded, filtered and the extract was kept until it was used. 15 g *Acacia Nilotica* was added to 15 ml deionized water, soaked all night, filtered and then the extract was kept until it was used. Equal volumes of the *Olea Europaea* fruit extract and *Acacia Nilotica* extract were mixed to prepare a mixed extract which preferably contains flavonoids, phenols and/or pentacyclic triterpenoids. 5 ml of the mixed extract was added to 50 ml of an aqueous solution of 0.1M $HAuCl_4$. Afterwards, the mixture was stirred for about 10 minutes at 35° C., or put in a shaker for 30 minutes at 145 rpm and 39° C., or put in a water bath shaking at 125 rpm and 60° C. or was left at room temperature for 3 months, approximately. A color change from yellow transparent to black and then to red purple indicated the formation of the respective gold nanoparticles.

A separation process for the extracts of *Olea Europaea* fruit extract and *Acacia Nilotica* extract, was carried out by using a reparatory funnel and separated fractions were tested by TLC. It was clearly found that effective groups or preparing the nanoparticles comprise flavonoids, phenols and/or pentacyclic triterpenoids. These effective groups are actually responsible and play main role as reducing and stabilizing agent for the rapid formation of nanorods with high monodispersity.

Figure 1:
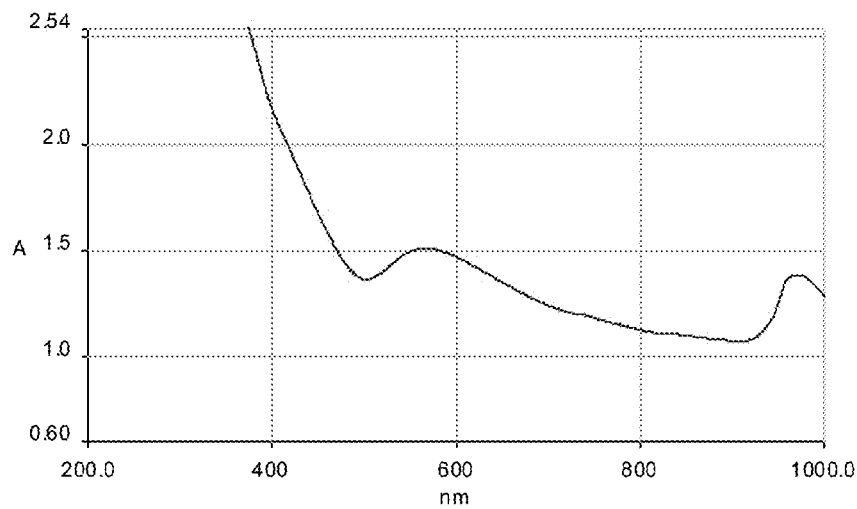
FIG. 1 shows a graph of UV-Vis spectrum of gold nanoparticles synthesized by the inventive method chemistry synthetic techniques according to example 1.
Figure 2:
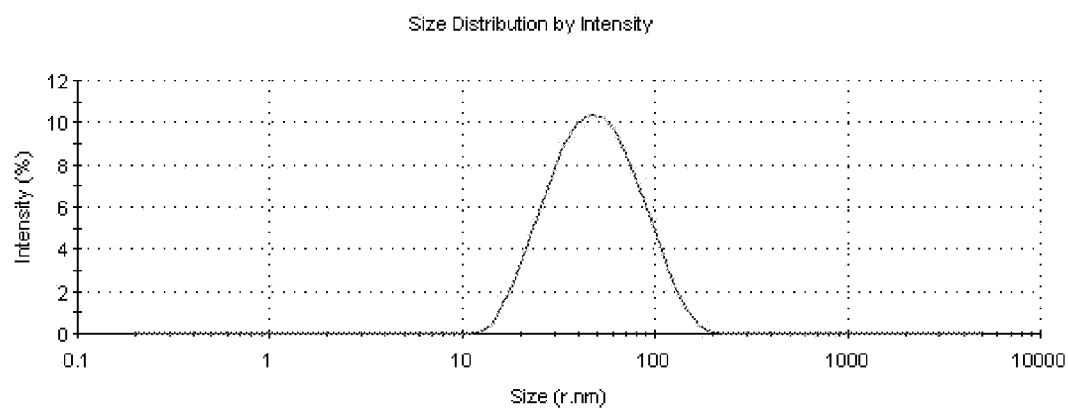
FIG. 2 shows a graph of Zetasizer® for measuring the average particle size of the gold nanoparticles prepared according to the invention.
Figure 3A:
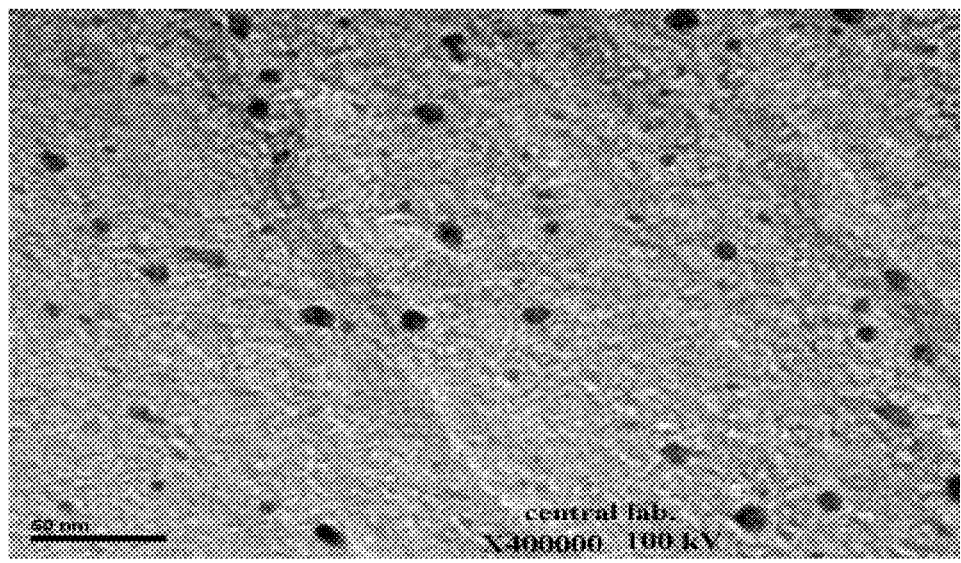
FIGS. 3a, 3b and 3c show a graph of transmission electron microscopy (TEM) image of gold nanoparticles synthesized by the inventive method (100 KV) with different shapes and magnifications.
Figure 3B:
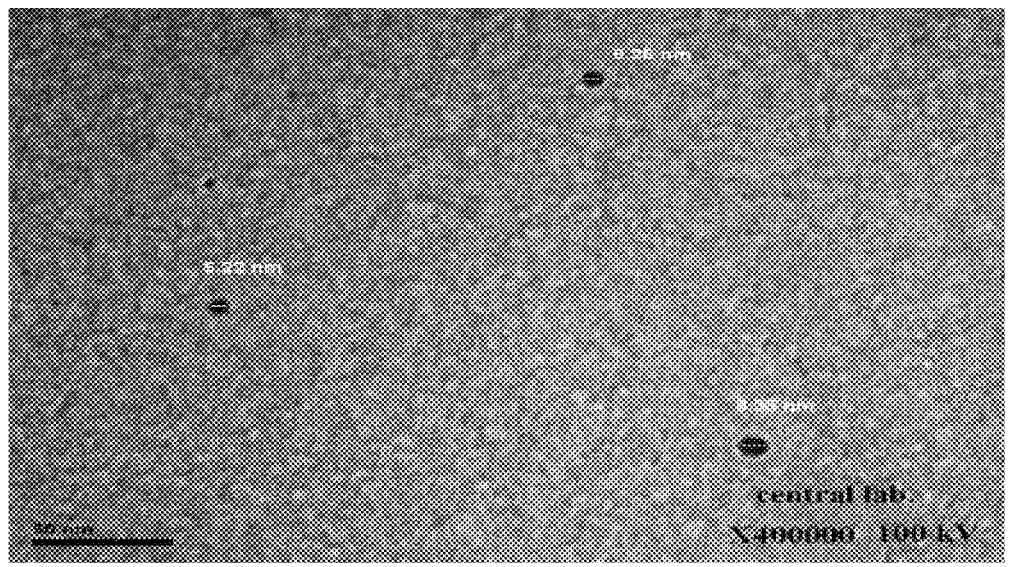
Figure 3C:
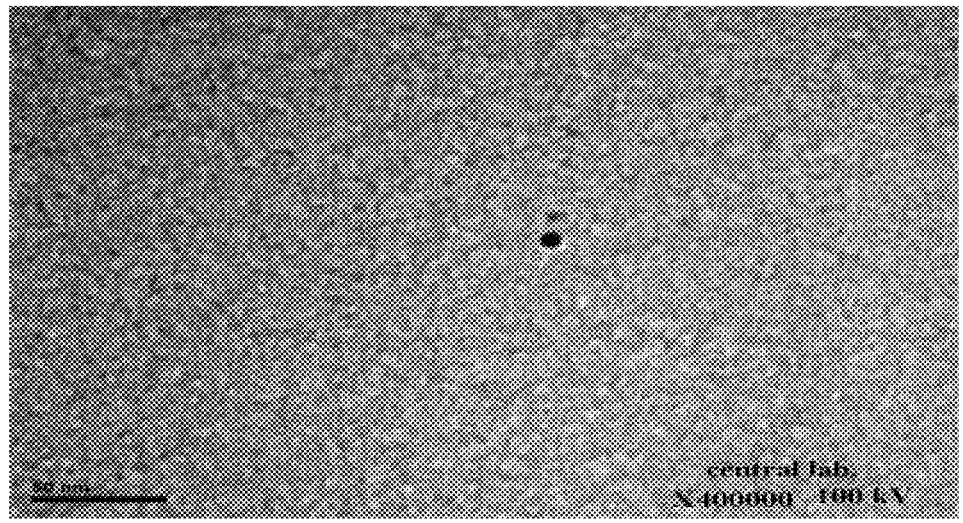
Figure 4:
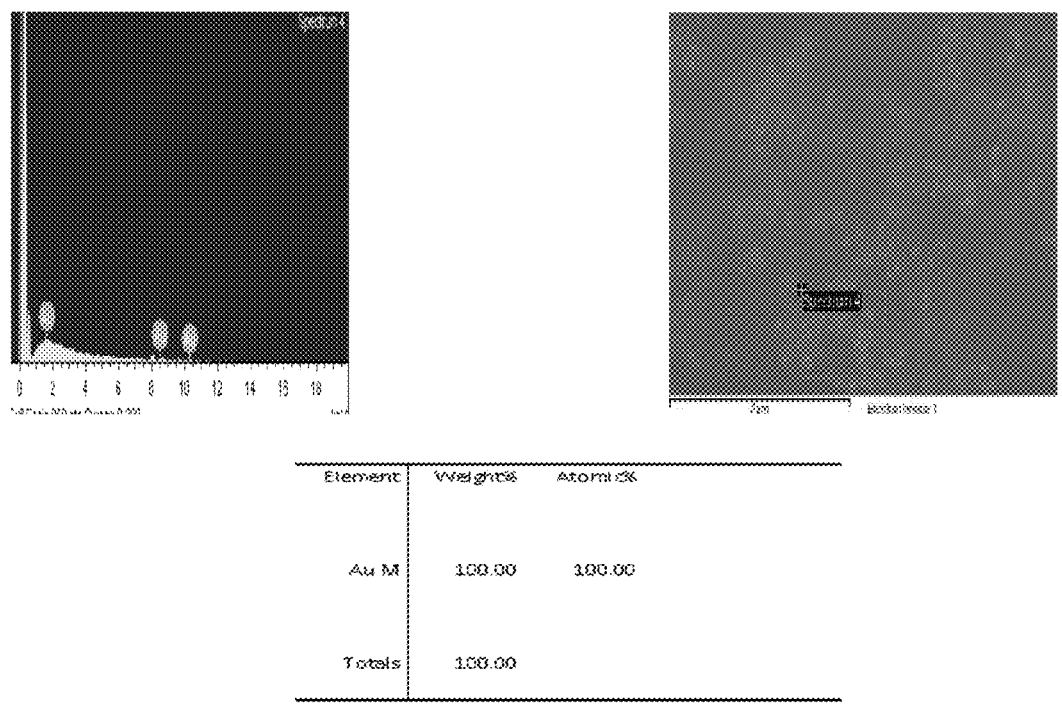
FIG. 4 shows the graph of scanning electron microscopy (SEM) image and elemental analysis by energy-dispersive spectroscopy (EDS) of the inventive gold nanoparticles.
Figure 5:
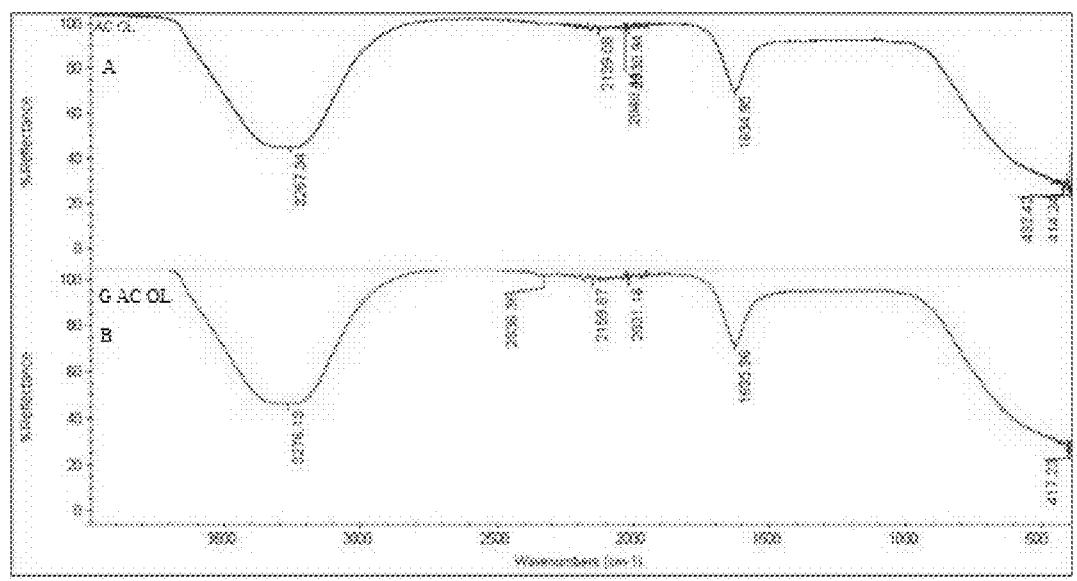
FIG. 5 shows a graph of FTIR spectrum of (A) mixed extract, (B) gold nanoparticles synthesized by the inventive method.

The formed gold nanoparticles have been analyzed: FIG. 1 shows the absorption peak (SPR) obtained in a visible range at 565.97 nm by UV-visible spectral analysis (Lambda 25, PerkinElmer, United Kingdom). This indicates monodisperse and colloidal gold nanoparticles. FIG. 2 shows that the average particle size of the gold nanoparticle is 40 nm, measured by Zetasizer® (ZEN 3600, MALVERN, United Kingdom). Transmission electron microscopy (TEM) (JEM-1011, JEOL, Japan) images of the prepared gold nanoparticles are shown in FIGS. 3a, 3b and 3c. The inorganic gold nanoparticles are spherical in shape with a smooth surface morphology. EDS spectrum, linked with SEM (JEOL-FE_SEM), was used to analyze the element of gold nanoparticles (FIG. 4), in addition with FTIR spectroscopy (NICOLET 6700, Thermo, USA) (FIG. 5). In this analysis, the electronic beam is focused only on the gold aggregates, so that the results can represent the real composition of a gold suspension. The EDS quantitative analysis confirmed the gold total elementary composition. To understand the above detailed description see graphics and images below.

Inoculation of Mice with Tumor Cells:

Female Swiss mice, 6-7 weeks of age, were obtained from the Laboratory Animal Unit of King Saud University, Research center—Saudi Arabia—Riyadh. Mice were injected subcutaneously in the flank of sub thigh with 200 μL (3×107) Ehrlich Ascites carcinoma cells suspended in 10 mM PBS. Near-infrared (NIR) plasmonic photothermal therapy (PPTT) was performed once tumor burden reached 10-12 mm in diameter (7-9 days).

In Vivo Near-Infrared PPTT:

100 microliters of the inventive gold nanoparticles (Laser $OD_{\lambda=808\ nm} = 40$) were directly injected into the tumor. Mouse tumors were extracorporeally exposed to NIR laser radiation (0.9-1.1 W/cm², 6 mm diameter, 10 min) within 2 min of injection to limit particle diffusion beyond the tumor boundaries. Due to the unusually rapid growth rates observed in the Ehrlich Ascites model, tumors and vital organs were harvested at days 11-14 for use in separate, ongoing the liver and kidney functions investigations.

Statistical Analysis

The results were expressed as mean (mean±SD), whereas SD is the standard derivation. Data were analyzed statistically using one-way analysis of variance followed by t test. A value of (P<0.05) was considered statistically significant.

Results:

1-Volume of Tumor:

TABLE 1

Average volume change in tumors followed by near-infrared PPTT at 808 nm irradiation of gold nanoparticles

| Time | 1 | 2 | 3 | 4 | 5 |
|---|---|---|---|---|---|
| First day(mm) | 10.8 | 12.1 | 5.6 | 9.7 | 11.5 |
| Sixth day (mm) | 9.6 | 8.9 | 1.7 | 4.1 | 6.3 |

The results of Table 1 clearly indicate specificity of near-infrared PPTT by reduction of the tumor volume when the inventive gold nanoparticles are directly injected.

2-Liver Function Changes:

TABLE 2

Liver function changes by treatment with the gold nanoparticles (NPs) and control group Healthy mice without tumor (Cont).

| Number of mice | 1 | 2 | 3 | 4 | 5 |
|---|---|---|---|---|---|
| GOT (NPs) U/l | 453 | 444 | 445 | 444 | 465 |
| GPT (NPs) U/l | 42.7 | 30.5 | 46.7 | 43.2 | 51.3 |
| GOT (Cont) U/l | 445 | 466 | 451 | 447 | 446 |
| GPT (Cont) U/l | 70.7 | 77.0 | 59.9 | 69.8 | 59.9 |

GPT and GOT are commonly measured to determine liver health. GPT (Glutamic-pyruvic transaminase), also known as ALT (Alanine aminotransferase), is a cytoplasmic hepatocellular enzyme, whose increase in blood is highly indicative for liver damage, e.g. by hepatitis, cirrhosis or hepatic tumors. GOT (Glutamic oxaloacetic transaminase) is applied as a marker for liver health as well. When measured for clinical data, the values for GPT and GOT are typically stated in units per liter (U/l).

TABLE 3

Unpaired t test (GPT) between two groups

| Group | Group (Control) | Group (NPs) |
|---|---|---|
| Mean | 41.8000 | 67.4600 |
| SD | 13.76989 | 7.43794 |
| SEM | 6.15808 | 3.32635 |
| N | 5 | 5 |

TABLE 4

Unpaired t test (GOT) between two groups:

| Group | Group (Control) | Group (NPs) |
|---|---|---|
| Mean | 376.0000 | 451.0000 |
| SD | 115.01739 | 8.68907 |
| SEM | 51.43734 | 3.88587 |
| N | 5 | 5 |

In Tables 3 and 4 the data for the unpaired t test for GPT and GOT measurements of Table 2 are shown, whereas SD is the standard derivation, SEM is the standard error of the mean and N is the sample size.

In conclusion, no significant changes of liver function among mice treated with gold nanoparticles (Np) and healthy mice (Cont) have been noticed by determine GPT. Unpaired t test results demonstrate that this difference is considered to be not statistically significant (95%) (t=−0.142−, df=8, standard error of difference=4.79677). Even for the determination of GOT, no significant changes of liver function has been observed. Unpaired t test results show that this difference is considered to be not statistically significant (95%) (t=2.006, df=8, standard error of difference=5.62).

3-Kidney Function Changes:

TABLE 5

Kidney function changes by treatment with the gold nanoparticles (NPs) and control healthy mice without tumor (Cont).

| Number of mice | 1 | 2 | 3 | 4 | 5 |
|---|---|---|---|---|---|
| Creatinine (NPs) mg/dl | <0.5 | <0.5 | <0.5 | <0.5 | <0.5 |
| Urea (NPs) | 61 | 70 | 53.2 | 48.1 | 118.3 |
| Creatinine mg/dl (Cont) | <0.5 | <0.5 | <0.5 | <0.5 | <0.5 |
| Urea(Cont) mg/dl | 38.1 | 46.4 | 44.8 | 46.5 | 47.3 |

Urea is a waste product formed of the digestion of proteins. Urea is usually passed in the urine. A high blood level of urea ("ureamia") indicates that the kidneys may not be working properly or that dehydration may occur (low body water content). Creatinine is a waste product made by the muscles. Creatinine passes into the bloodstream, and is usually passed out in urine. A high blood level of creatinine indicates that the kidneys may not be working properly. Creatinine is usually a more accurate marker of kidney function than urea. Typically, urea and creatinine are reported in milligrams per deciliter (mg/dl).

TABLE 6

Unpaired t test (Urea) between two groups

| Group | Group (Control) | Group (NPs) |
|---|---|---|
| Mean | 66.4200 | 44.6200 |
| SD | 10.05967 | 3.75593 |
| SEM | 4.49882 | 1.67970 |
| N | 5 | 5 |

Changes of some kidney functions determined by creatinine and urea showed no differences among mice treated with gold nanoparticles (Np) and healthy mice (Cont), as shown in Tables 5 and 6. For the urea testing, the unpaired t test results of Table 6 demonstrate that this difference is considered to be not statistically significant (95%) (t=2.006, df=8, standard error of difference=12.71239). Table 5 shows the same results for creatinine From all of these results, the benefit of the inventive method and the inventive nanoparticles prepared by using green chemistry synthetic techniques, comprising the mixed extract of *Olea Europaea* fruit extract and *Acacia Nilotica* extract, is demonstrated. The benefit is especially the significant affinity of the inventive nanoparticles towards Ehrlich Ascites carcinoma cell.

Similar studies has been considered by E. B. Dickerson et al., 2008, who presented a work which demonstrates the feasibility of in-vivo PPTT treatment of deep-tissue malignancies using easily-prepared plasmonic gold nanorods and a small, portable, inexpensive near-infrared (NIR) laser. Dramatic size decreases in squamous cell carcinoma xenografts were observed for direct (P<0.0001) and intravenous (P<0.0008) administration of pegylated gold nanorods with resorption of >57% of the directly-injected tumors and 25% of the intravenously-treated tumors. The significant benefit of the present invention compared to these studies is that using green natural material to synthesize gold nanoparticles as anti-cancer agents, yields in a better treatment of Ehrlich Ascites carcinoma cell.

Moo-Sung Kim et al., 2013, reported in-vitro studies for investigating the antioxidative and anti-neuroinflammatory potentials of *Olea Europaea* Linn. fruit pulp (OFP-EA) extract in LPS-stimulated BV-2 microglial cells. The results indicate that OFP-EA extract exhibited strong antioxidant properties.

Example 2

Figure 6:
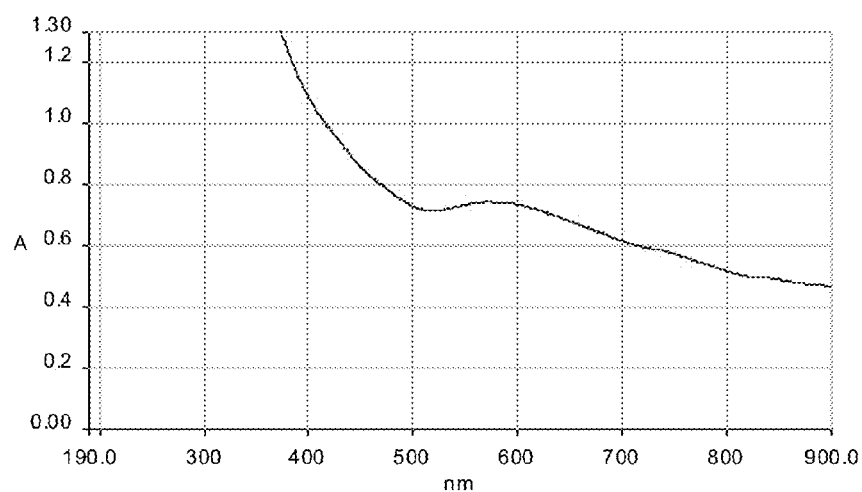
FIG. 6 presents a graph of UV-Vis spectrum of gold nanorods prepared according to the present invention, example 2.
Figure 9:
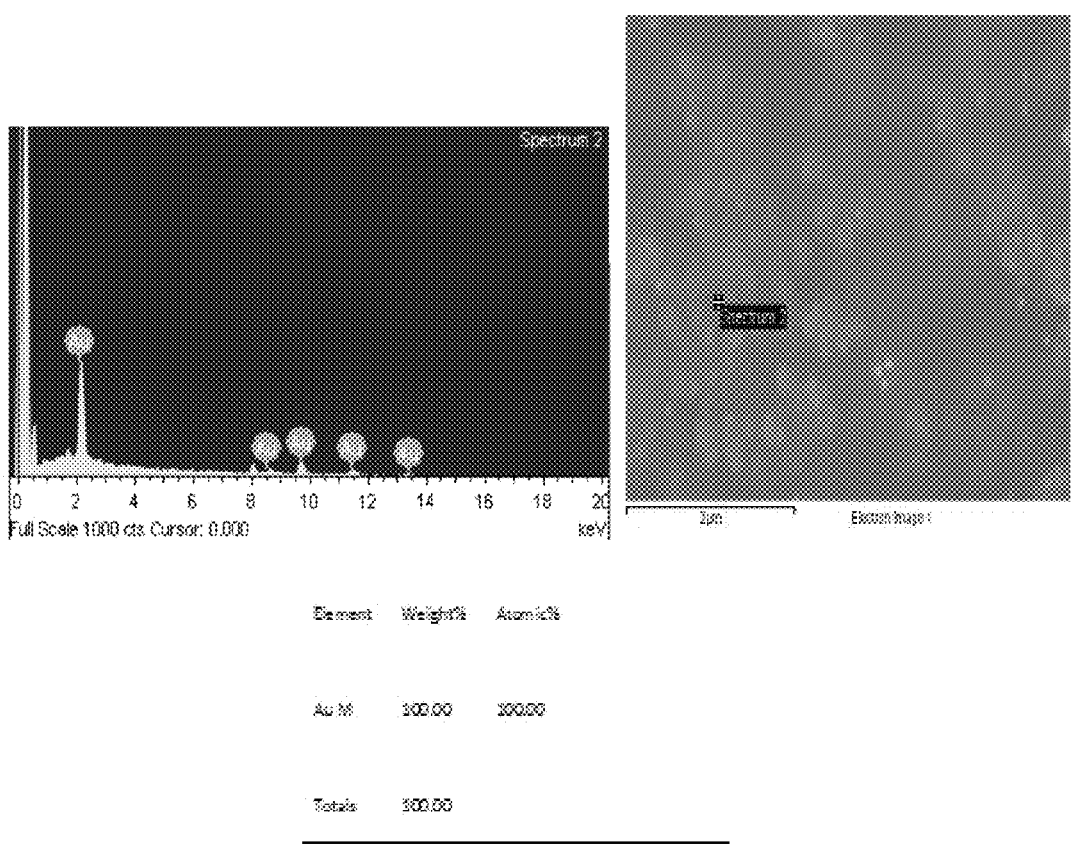
FIG. 9 presents a graph of a scanning electron microscopy (SEM) image and elemental analysis by energy-dispersive spectroscopy (EDS) of gold nanorods prepared according to the present invention, example 2.
Figure 10:
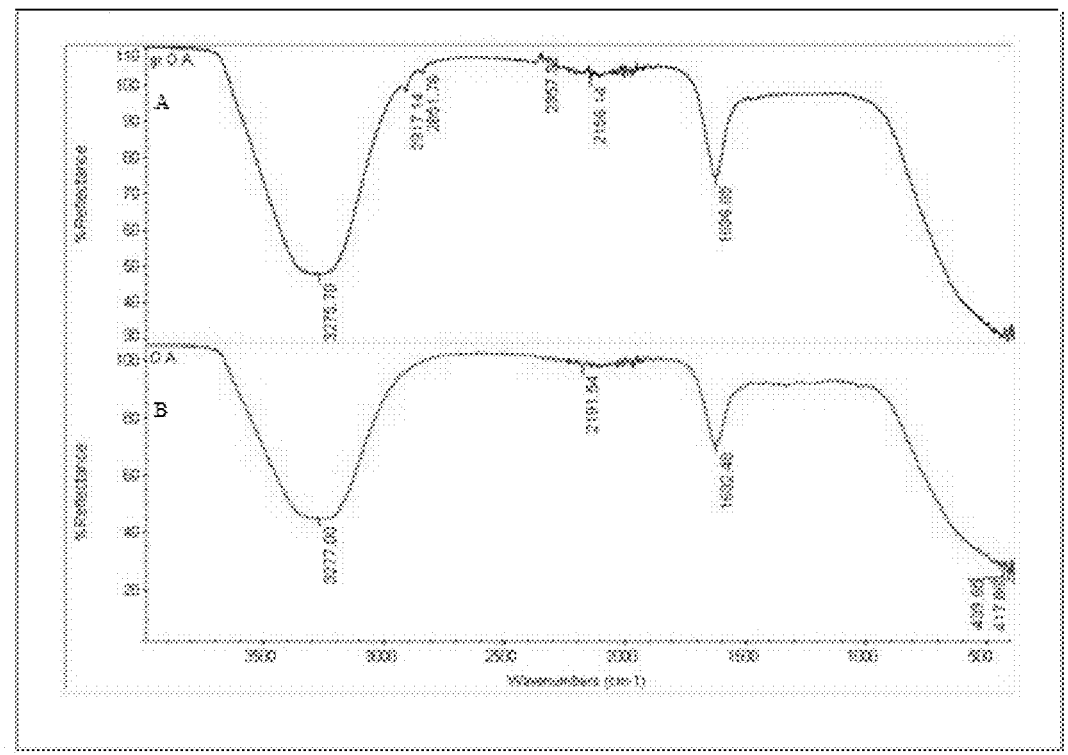
FIG. 10 presents a graph of a FTIR spectrum of inventive (A) gold nanorods synthesized by the inventive method, (B) mixed extract.
Figure 11:
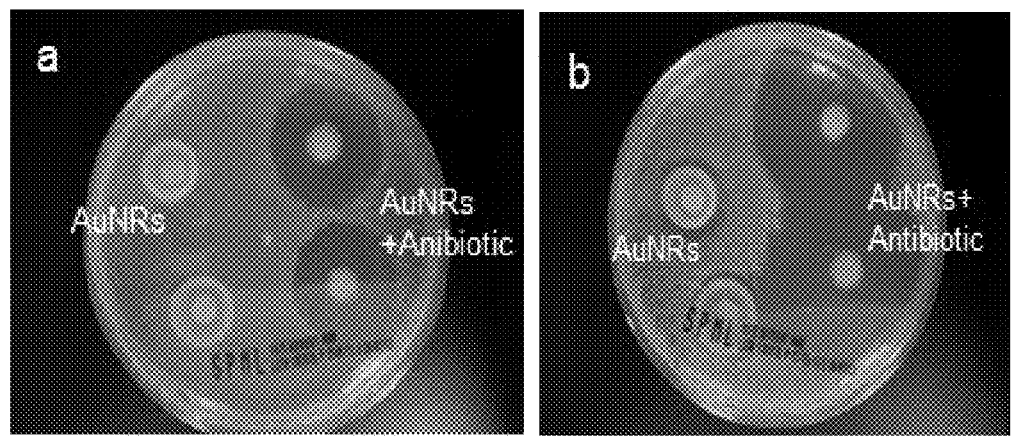
FIG. 11 presents a graph of Antibacterial activity assay of eco-friendly gold nanorods and with antibiotic (5, 10 μg/ml) respectively against (a) *E. coli* and (b) *Staphylococcus aureus*.

Noble metal colloidal gold nanorods were synthesized by bioreduction of $AuCl_4^-$ ions. 15 g *Olea Europaea* fruit was washed carefully and was then added to 15 ml deionized water. Then it was grinded, filtered and kept until used. 15 g *Acacia Neurotica* was added to 15 ml deionized water, soaked all night, filtered and then the extract was kept until it was used. Equal volumes of the *Olea Europaea* fruit extract and *Acacia Neurotica* extract were mixed to prepare a mixed extract which preferably contains flavonoids, phenols and/or pentacyclic triterpenoids. 5 ml of the mixed extract was added to 50 ml of an aqueous solution of 0.09M $HAuCl_4$ and cetyl trimethylammonium bromide (CTAB) 0.35M. This has been stirred for about 10 minutes at 35° C. When adding the extract the color changed, from orange transparent to colorless, then dropping one or more drop of NaOH 0.5M, these colorless indicated the formation of the respective nanorods. Au antibacterial test of the gold nanorods has been conducted, showing a significant inhibition against both gram-positive and gram-negative bacteria. As a reference, nanoparticles were also prepared by using an organic extract as described in the prior art. The formed nanorods have been analyzed: FIG. 6 shows the absorption peak (SPR) obtained in the visible range at range at 515.04-560 nm by UV-visible spectral analysis (Lambda 25, PerkinElmer, United Kingdom) This indicates mono disperse gold nanorods. FIG. 7 shows that the particles average size is 96 nm, measured by Zetasizer® (ZEN 3600, MALVERN, United Kingdom). Transmission electron microscopy (TEM) (JEM-1011, JEOL, Japan) images of prepared gold nanorods are shown in the FIGS. 8a, 8b, 8c. The gold nanorods are rods in shape with a smooth surface morphology. EDS spectrum, linked with SEM (JEOL-FE_SEM), was used to analyze the element of gold nanoparticles (FIG. 9). In this analysis, the electronic beam is focused only on the gold aggregates, so the results can represent the real composition of a gold suspension. The EDS quantitative analysis confirmed the gold total elementary composition, in addition of FTIR spectroscopy (NICOLET 6700, Thermo, USA), FIG. 10.

Microorganisms and Antibacterial Activity

Pure culture of *Escherichia coli, Staphylococcus aureus, Kleb* sp., *Pseudomonas* sp., *Salmonella* sp., and *Streptococcus* of bacteria were used. The antibacterial activities of biosynthesized gold nanorods nanoparticles were carried out by disc diffusion method. Nutrient agar medium plates were prepared, sterilized and solidified. After solidification bacterial cultures were swabbed on these plates. The sterile discs were dipped in gold nanorods nanoparticle solutions (1, 5, 10 µg/ml) and placed in the nutrient agar plate and kept for incubation at 37° C. for 24 hours, upon inhibitory activity a zone of clearing around the wells was observed. The diameter of the clearing zones was measured in mm using the ruler scale. The experiments were repeated 3 times and mean values of zone diameter were presented (N. Savithramma et al., 2011).

Results:

TABLE 7

Zone of inhibition (mm) of gold nanorods prepared according to example 2, against different bacterial strains.

| | Reagents | | | |
|---|---|---|---|---|
| | *E coli* Interpretation zone diameters (mm) | | *Staphylococcus aureus* Interpretation zone diameters (mm) | |
| | Concentrations | | | |
| | 5 µg/ml | 10 µg/ml | 5 µg/ml | 10 µg/ml |
| Gold nanorods | 15 | 16 | 19 | 24 |
| Gold nanorods antibiotic | 27 | 30 | 40 | 45 |

Example 3

Colloidal silver nanoparticles were synthesized by bioreduction of $Ag^+$ ions. 15 g *Olea Europaea* fruit was washed carefully and was added to 15 ml deionized water. Then it was grinded, filtered and the extract was kept until it was used. 15 g *Acacia Nilotica* was added to 15 ml deionized water, soaked all night, filtered and then the extract was kept until it was used. The *Olea Europaea* fruit extract and *Acacia Nilotica* extract were mixed to prepare a mixed extract which preferably contains flavonoids, phenols and/or pentacyclic triterpenoids. 5 ml of the mixed extract was added to 50 ml of an aqueous solution of 0.1M $Ag(NO_3)_2$. Afterwards, the mixture was stirred for about 10 minutes at 35° C., or put in a shaker for 30 minutes at 145 rpm and 39° C., or put in a water bath shaking at 125 rpm and 60° C. or was left at room temperature. The color change from colorless transparent to brown indicated the formation of the respective silver nanoparticles.

A separation process for extracts of *Olea Europaea* fruit extract and *Acacia Nilotica* extract, was carried out by using a separatory funnel and separated fractions were tested by TLC. It was clearly found that effective groups or preparing the nanoparticles comprise flavonoids, phenols and/or pentacyclic triterpenoids. These effective groups are actually responsible and play main role as reducing and stabilizing agent for the rapid formation of nanorods with high monodispersity.

Figure 12:
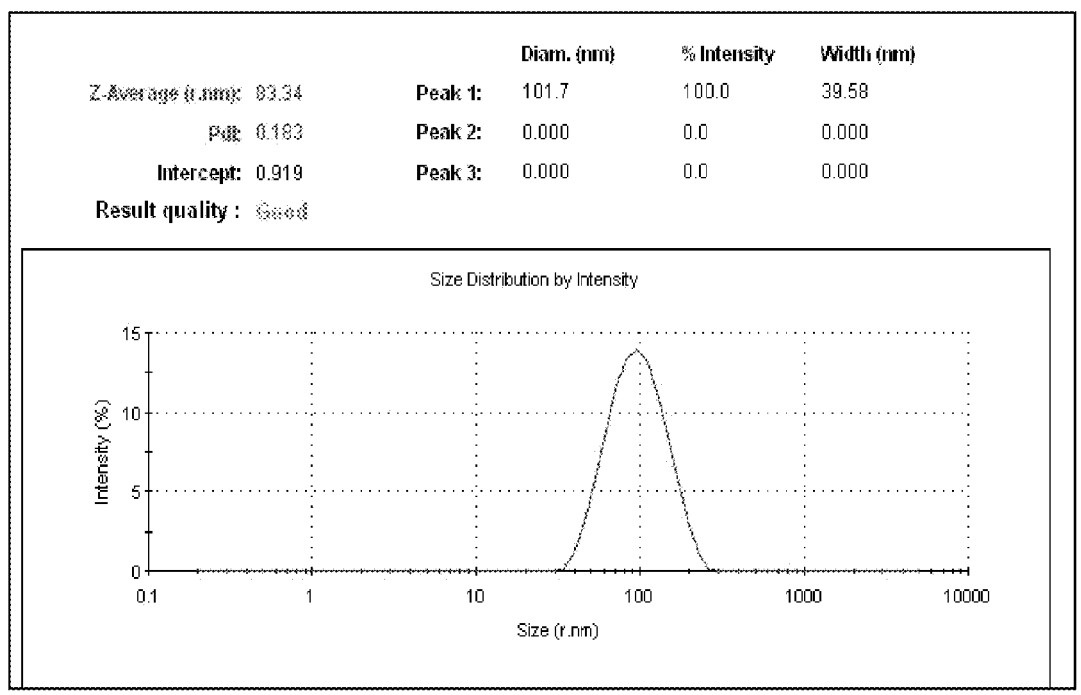
FIG. 12 shows a graph of Zetasizer® for measuring the average particle size of the silver nanoparticles prepared according to the present invention.
Figure 13A:
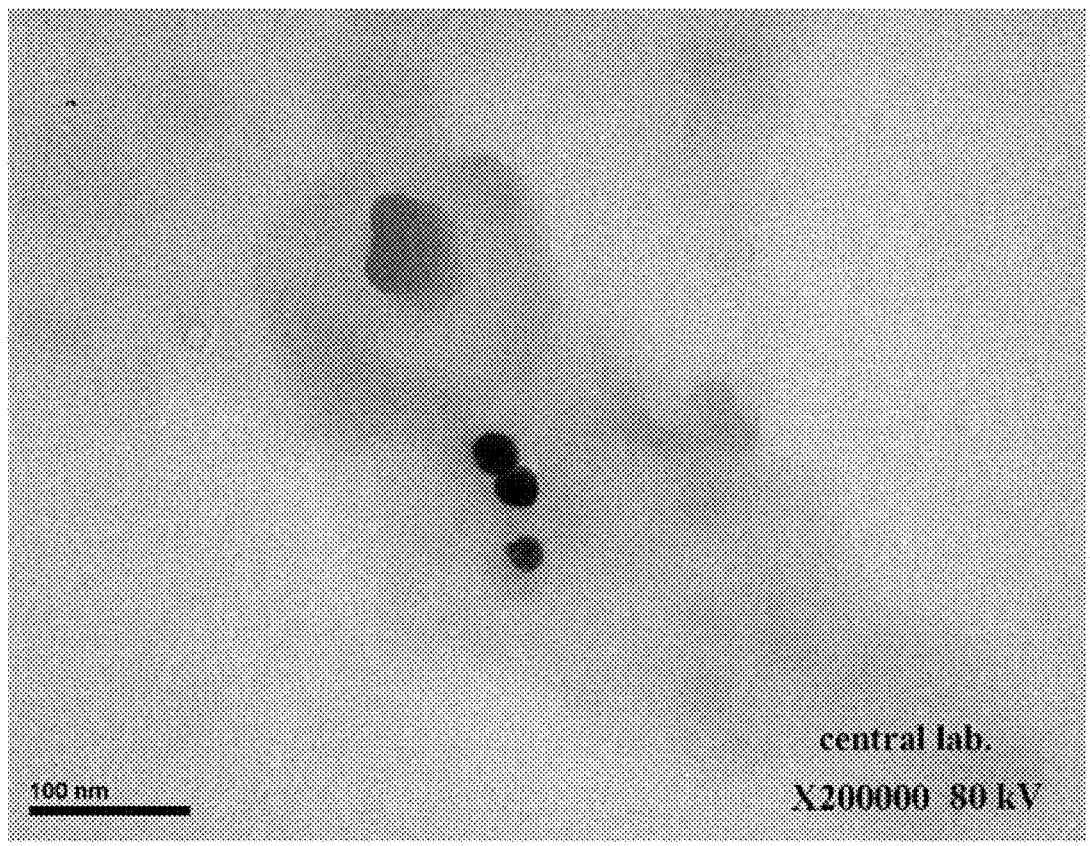
FIGS. 13a, 13b and 13c show a graph of transmission electron microscopy (TEM) image of silver nanoparticles synthesized by the inventive method (100 KV) with different shapes and magnifications.
Figure 13B:
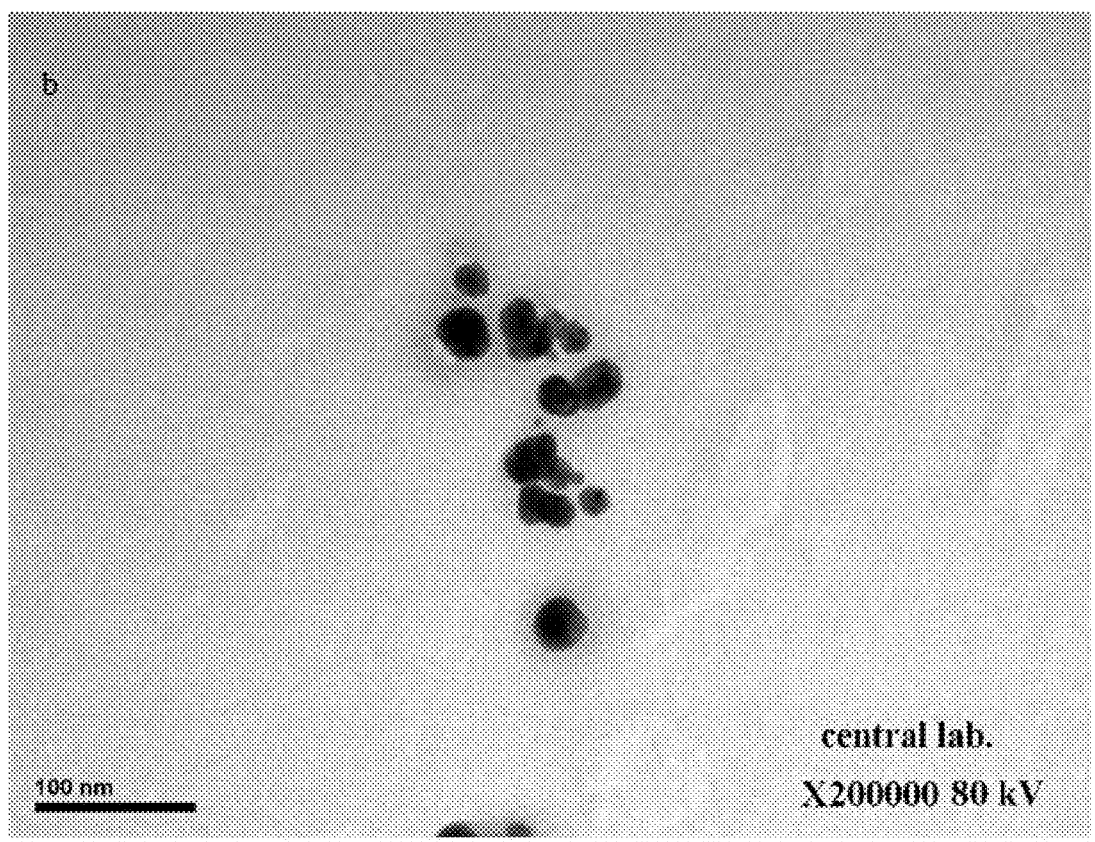
Figure 13C:
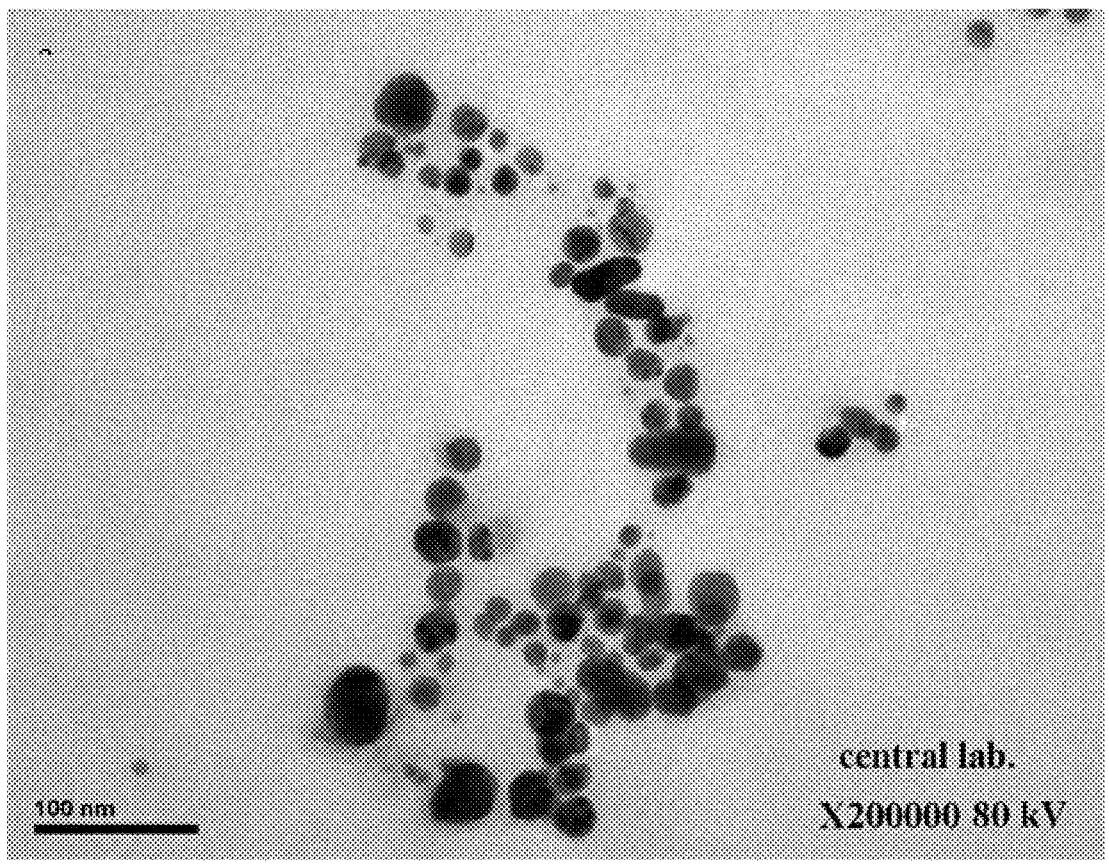
Figure 14:
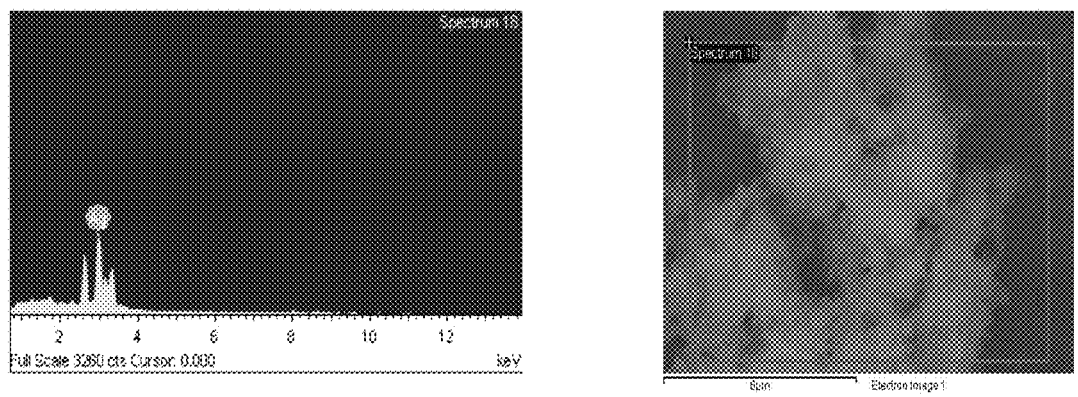
FIG. 14 shows the graph of scanning electron microscopy (SEM) image and elemental analysis by energy-dispersive spectroscopy (EDS) of the inventive silver nanoparticles.
Figure 15A:
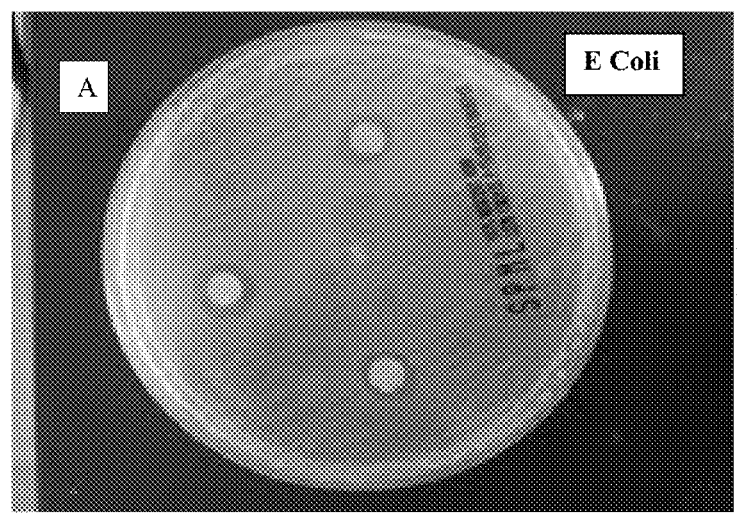
FIGS. 15a, 15b and 15c Antibacterial activity assay for green Ag nanoparticles prepared according to the present invention against, (A) *E. Coli* (B) *Staphylococcus aureus*, (C) *Streptococcus*.
Figure 15B:
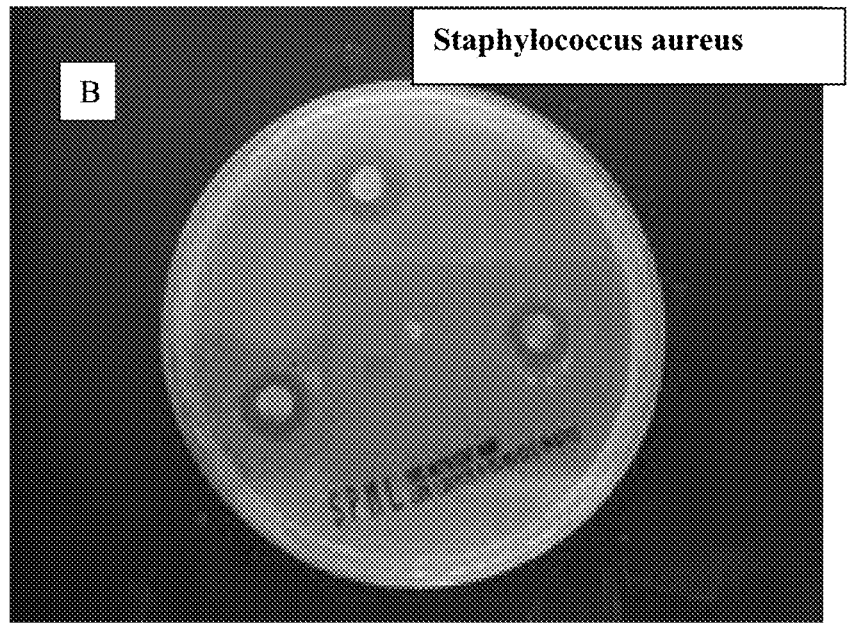
Figure 15C:
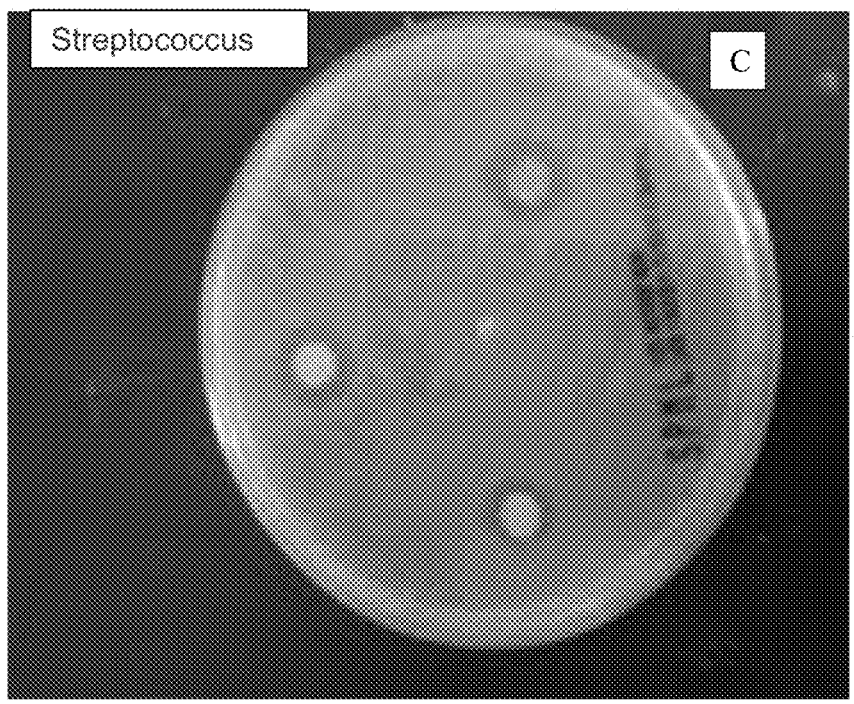

The formed silver nanoparticles have been analyzed: FIG. 12 shows that the average particle size of the silver nanoparticle is 83 nm, measured by Zetasizer® (ZEN 3600, MALVERN, United Kingdom). Transmission electron microscopy (TEM) (JEM-1011, JEOL, Japan) images of the prepared silver nanoparticles are shown in FIGS. 13a, 13b and 13c. The inorganic silver nanoparticles have different shapes like spherical, rod and other shapes as shown in FIG. 13. EDS spectrum, linked with SEM (JEOL-FE_SEM), was used to analyze the element of silver nanoparticles (FIG. 14). The EDS quantitative analysis confirmed the silver total elementary composition.

Microorganisms and Antibacterial Activity

The antibacterial test of silver nanoparticles, prepared using a 1:3 mixture of *Olea Europaea* fruit extract and *Acacia Nilotica* extract with silver nitrate under stirring, showed a significant inhibition against both gram-positive and gram-negative bacteria.

Pure culture of *Escherichia coli, Staphylococcus aureus,* and *Streptococcus* of bacteria were used. The antibacterial activities of biosynthesized silver nanoparticles were carried out by disc diffusion method. Nutrient agar medium plates were prepared, sterilized and solidified. After solidification bacterial cultures were swabbed on these plates. The sterile discs were dipped in silver nanoparticle solutions (5, 10,15 µg/ml) and placed in the nutrient agar plate and kept for incubation at 37° C. for 24 hours, upon inhibitory activity a zone of clearing around the wells was observed. The diameter of the clearing zones was measured in mm using the ruler scale. The experiments were repeated 3 times and mean values of zone diameter were presented (N. Savithramma et al., 2011).

Results:

TABLE 8

Zone of inhibition (mm) of silver nanoparticles, prepared according to the present invention, against different bacterial strains.

| | Reagents | | | | | | | | |
|---|---|---|---|---|---|---|---|---|---|
| | *E coli* Interpretation zone diameters (mm) | | | *Staphylococcus aureus* Interpretation zone diameters (mm) | | | *Streptococcus* Interpretation zone diameters (mm) | | |
| | Concentrations µg/ml | | | | | | | | |
| | 5 | 10 | 15 | 5 | 10 | 15 | 5 | 10 | 15 |
| Silver Nanoparticles | 10 | 12 | 14 | 12 | 14 | 17 | 12 | 13 | 15 |

The features disclosed in the foregoing description, the claims and the drawings may, both separately or in any combination, be material for realizing the invention in diverse forms thereof.

The invention claimed is:

1. Method for preparing noble metal nanoparticles, comprising the following steps:
   a) preparing an *Olea Europaea* fruit extract
   b) preparing an *Acacia Nilotica* extract
   c) mixing the *Olea Europaea* fruit extract and the *Acacia Nilotica* extract for preparing a mixed extract
   d) providing an aqueous solution containing a noble metal compound dissolved therein
   e) mixing the mixed extract obtained in step c) and the aqueous solution of step
   d) to form noble metal nanoparticles.

2. Method according to claim 1, wherein the mixed extract obtained in step c) contains flavonoids, phenols and/or pentacyclic triterpenoids.

3. Method according to claim 1, wherein the preparation of the *Olea Europaea* fruit extract is performed by adding deionized or distilled water to *Olea Europaea* fruit.

4. Method according to claim 1, wherein the preparation of the *Acacia Nilotica* extract is performed by adding deionized or distilled water to *Acacia Nilotica*.

5. Method according to claim 1, wherein the *Olea Europaea* fruit extract and the *Acacia Nilotica* extract are mixed in a range of mixing ratios from 5:1 to 1:5.

6. Method according to claim 1, wherein the mixing of step e) is at room temperature.

7. Method according to claim 1, wherein the noble metal is Au or Ag.

8. Method according to claim 7, wherein the noble metal compound is chloroauric acid.

9. Method according to claim 1, wherein the aqueous solution provided in step d) also comprises a surfactant.

10. Noble metal nanoparticles prepared by the method of claim 1, wherein the average particle size is within a range of 10-100 nm.

11. Noble metal nanoparticles according to claim 10, wherein the noble metal nanoparticles are substantially spherical.

12. Noble metal nanoparticles according to claim 10, wherein the noble metal nanoparticles are substantially monodispersed.

13. Noble metal nanoparticles according to claim 10, wherein the nanoparticles are colloidal.

14. A method of antibacterial and/or cancer treatment, comprising administering to an animal in need thereof the nanoparticles prepared by the method of claim 1.

15. The method of claim 14, wherein the nanoparticles are administered with photothermal therapy in treatment of Ehrlich Ascites carcinoma cells.

16. The method of claim 9 wherein the surfactant is cetyl trimethyl ammonium bromide (CTAB).

* * * * *